US00PP14578P29

(12) United States Plant Patent
Colfer

(10) Patent No.: US PP14,578 P2
(45) Date of Patent: Mar. 9, 2004

(54) ARTICHOKE PLANT NAMED 'PS-MSC0003'

(50) Latin Name: *Cynara scolymus L.*
Varietal Denomination: PS-MSC0003

(75) Inventor: William J. Colfer, Aptos, CA (US)

(73) Assignee: Plant Sciences, Inc., Watsonville, CA (US)

( * ) Notice: Subject to any disclaimer, the term of this patent is extended or adjusted under 35 U.S.C. 154(b) by 32 days.

(21) Appl. No.: 10/251,982

(22) Filed: Sep. 23, 2002

(51) Int. Cl.[7] ..... A01H 5/00
(52) U.S. Cl. ..... Plt./258

(58) Field of Search ..... Plt./258

(56) References Cited

U.S. PATENT DOCUMENTS

PP12,210 P2 * 11/2001 Colfer ..... Plt./258

* cited by examiner

*Primary Examiner*—Bruce R. Campell
*Assistant Examiner*—W C Haas
(74) *Attorney, Agent, or Firm*—Foley & Lardner

(57) ABSTRACT

A new and distinct cultivar of artichoke plant named 'PS-MSC0003', characterized by male sterility, large head size, fleshiness of bracts, fleshiness of hearts, uniformity of head shapes.

3 Drawing Sheets

Latin name of the genus and species of the plant claimed: *Cynara scolymus L.*
Variety denomination: PS-MSC0003.

BACKGROUND OF THE INVENTION

The present invention comprises a new and distinct cultivar of artichoke plant, botanically known as *Cynara scolymus L.* and herein referred to by the cultivar name 'PS-MSC0003'.

*Cynara scolymus L.*, commonly known as Globe artichoke, is a thistle-like perennial herb and is a member of the family Asteraceae. Globe artichokes comprise leaves which are pinnately lobed but primarily spineless, globose capitula composed of overlapping layers of large volucral bracts, and receptables which are enlarged and fleshy. Globe artichoke plants may be propagated by division and are essentially grown for the production of the immature flower heads, which are considered as vegetable delicacies. Fresh artichokes may be steamed or boiled, after which the fleshy receptacle, inner and outer bracts, and parts of the floral stem may be eaten.

BRIEF SUMMARY OF THE INVENTION

The new cultivar is a product of a planned breeding program carried out by the inventor, William J. Colfer at Chowchilla, Calif. in 1997. The female parent is CTC6 (seed parent). The male parent is an unknown cultivar selected from an open-pollinated breeding plot. The new cultivar was discovered from the progeny of the stated cross by William J. Colfer and was asexually propagated for the first time in 1997 in Watsonville, Calif.

Asexual propagation by division has demonstrated the stability of the combination of characteristics of the new cultivar from generation to generation.

The new cultivar has not been observed under all possible environmental conditions. The phenotype may vary with variations in environment such as temperature, light intensity and daylength, without any change in the genotype of the cultivar.

BRIEF DESCRIPTION OF THE DRAWINGS

The accompanying photographic drawing shows fruit and leaves from a typical specimen plant of 'PS-MSC0003', with color being depicted as possible with illustrations of this type.

The first drawing is a side view of the fruit and foliage of 'PS-MSC0003'.

The second drawing is a close-up view of the fruit showing its physical dimensions.

The third drawing is a close-up view showing a vertical cross-section of the fruit.

DETAILED BOTANICAL DESCRIPTION

The following observations, measurements and values describe plants of 'PS-MSC0003' grown in Chowchilla, Calif. under conditions which closely approximate those generally used in horticultural practice. The age of the plants described is approximately 355 days (235 days from transplanting and an additional 120 days developed in transplant trays).

All color references below are measured against The Munsell Book of Color, Munsell Color Macbeth Division of Kollomogen Corporation. Colors are approximate as color depends on horticultural practices such as light level and fertilization rate, among others.

Chowchilla is located in California's central San Juaquin valley. Conditions can vary greatly during the summer months. Air temperature can range between the low 20's (degrees Fahrenheit) in the winter to well above the 100 (degrees Fahrenheit) during the summer months. Relative humidity is generally low with values ranging from the mid 40's to the high 60's. Prevailing winds are westerly and rainfall rarely exceeds 15" (inches) of rainfall.

In the following description, holding quality was measured by the physical appearance of the harvested heads. This includes the heads appearance following 3, 7 and 10 day storage periods in a cold storage room held at 34 (degrees Fahrenheit). Head exterior (oxidation) was observed at each of the three observation points. Browning and blackening of plant tissue was evaluated as light, moderate and extreme. Juiciness was measured by observing exudate and rated as absent, moderate or excessive. Overall storage response was measured by observations concentrated on visible color variability and/or presence of lesions or other cosemetic anomalies. Leaf ratio (L/W) was determined by dividing representative leaf sample length measurements by representative leaf sample width measurements. Finally, head response to (weather) was determined by observing the heads at maturity. These field observations focus on presence or absence of bronzing, necrotic and chlorotic lesions or any abiotic response to environmental conditions. These data are reported as the possible causal event(s) and then describe the detailed head and plant responses.

It should be noted that these data were collected from first year tissue culture outplants. These data are subject to change in the plant's future growth and development. The new and distinct cultivar of artichoke plant named 'PS-MSC0003' is characterized by:

1. male sterility;
2. large head size;
3. fleshiness of bracts;
4. fleshiness of hearts; and
5. uniformity of head shapes.

The date of first harvest is approximately May 31 and the date of final harvest is approximately June 31, depending on environmental conditions. Plant growth from November to February is moderate, depending upon environmental and agronomic conditions. Plant growth and development from March to June is rapid, depending upon environmental and agronomic conditions, with sexual stages initiating early May.

TABLE 1

| | |
|---|---|
| Parentage: | |
| Female parent: | CTC6 (Seed parent) |
| Classification: | Botanical: *Cynara scolymus* L.<br>Commercial: artichoke c.v. PS-MSC0003 |
| Propagation: | Asexual production either by tissue culture (standard micropropagation methodology) or division. |
| Plant: | |
| Height: | $\bar{x}$ = 147.32 cm<br>range: 132.08–165.10 cm |
| Growth Habit: | Upright, broad |
| Dimensions: | $\bar{x}$ = 147.32 cm (h) × 177.29 cm (w)<br>range: 132.08–165.10 cm (h) × 160.02–198 cm (w) |
| Side Shoots: | $\bar{x}$ = 1.40<br>range: 1.0–2.0 shoots |
| Length of Side Shoots: | Between 20–30.5 cm |
| Diameter of Side Shoots: | Between 4.8–7.2 cm |
| Foliage Density: | Moderate. Same variability is visible, but canopy is generally "open". |
| Side Shoot Development: | Side shoot development is moderate but vigorous. |
| Number of leaves on Side Shoots: | Between 6–8 |
| Main Stem Length: | Between 37–60 cm |
| Diameter of Main Stem: | Between 4.7–6.4 cm |
| Number of Leaves on Main Stem: | Between 14–28 |
| Capitulum: | |
| Size: | Primary: 33.66–35.56 cm<br>Secondary: 26.04–27.94 cm |

TABLE 1-continued

| | |
|---|---|
| Shape: | Oval. Head shape is highly uniform. Very little variation was observed. |
| Number: | $\bar{x}$ = 7.70/plant<br>range: 5.0–11.0 heads/plant |
| Texture: | Intermediate. Smooth. |
| Fragrance: | Mild, lightly aromatic |
| Bract Size: | $\bar{x}$ = 7.39 cm (l) × 6.38 cm (w)<br>range: 7.0–7.9 cm (l) × 5.9–6.6 cm (w) |
| Bract Shape: | Bracts are predominantly oval shaped, some intermediate bracts are slightly rounded. |
| Bract Texture: | Smooth, slight texture. |
| Bract Number: | $\bar{x}$ = 63.00<br>range: 60–66 bracts. |
| Bract Color: | Inner: 5 GY 9/1–2.5 GY 9/2–10 Y 9/4–10 Y 9/6 range on inner bracts varies<br>Outer: 5 GY 4/4 |
| Bract Basal Thickness: | $\bar{x}$ = 7.37 mm<br>range: 5.0–9.0 mm |
| Heart Description: | Concave/full. Hearts are well developed with thick outer regions. |
| Heart Color: | 7.5 Y 9/2–10 Y 9/2. Heart coloration is white, but oxidizes to yellow hues rapidly. |
| Papus Length: | $\bar{x}$ = 7.40 mm<br>range: 5.0–10.0 mm |
| Papus Color: | Variable white coloration. |
| Overall Cold Storage Response: | Good cold storage response. Some light oxidation observed. |
| Head Firmness: | Heads are firm. |
| Bract Firmness: | Moderate. Bracts lack flexibility and a malleable quality. |
| Gloss: | Dull appearance. Heads and outer bracts lack gloss except for slight glossiness just below the spines. |
| Cold Storage (hold quality): | Good head response to cold storage. |
| Head Exterior (oxidation): | Head experienced only light oxidation, no necrotic tissue was observed. |
| Juiciness: | Moderate presence. Stems are moist and some free moisture is visible. |
| Head Response (weather): | No adverse environmental head responses were observed. |
| Bud Burst: | Between May 12 and June 25 |
| Bud Weight: | Between 443.65 and 462.90 grams; average 457.73 grams per head |
| Bloom Time: | June 3 and June 30 |
| Bloom Duration: | Approximately 42 days |
| Bloom Diameter: | Between 10–13.2 cm |
| Bloom Depth: | Between 12–13.4 cm |
| Bloom Shape: | Head (slightly flattened oval) |
| Floret Number per Bloom: | Approximately 1372 to 1436 |
| Floret Size: | Between 7.5–8.1 cm in length<br>Between 3 and 3.2 mm in width |
| Floret Color: | Range between 2.5P 7/4–2.5P 5/8–2.5P 4/10–2.5P 4/8 |
| Seeds: | |
| Shape: | Ovate |
| Size: | 0.6–0.7 mm in length; 0.3–0.4 mm in width |
| Number: | Highly variable between 43–590; average 232 seeds per head |
| Coloration: | Variable; light brown hues with dark speckling; some gray and green hues with speckled pattern |
| Foliage: | |
| Shape: | Irregularly dentate, pinnatisect, reduced tomentose and mucronulate |
| Length: | $\bar{x}$ = 104.05 cm<br>range: 95.1–117.1 cm |
| Width: | $\bar{x}$ = 60.08 cm<br>range: 54.3–64.2 cm |
| Leaf Serrations: | $\bar{x}$ = 53.89 mm<br>range: 47.8–58.7 mm |
| Leaf Basal Angle: | $\bar{x}$ = 38.08 degrees<br>range: 25–45 degrees |

TABLE 1-continued

| | |
|---|---|
| Leaf Ratio (L/W): | $\bar{x}$ = 1.73<br>range: 1.50–2.05 |
| Leaf Area: | $\bar{x}$ = 6,250.96 $cm^2$<br>range: 5543.32–7275.43 $cm^2$ |
| Color: | 5 GY 3/4–5 GY 3/6–5 GY 4/4 |
| Texture: | Moderate, rough. Uniform "blister-like" appearance. Raised portions are not uniform in size or shape. |
| Veination: | Intermediate greenish. Midvein is distinct, but not prominent. |
| Pubescence: | Sparse. Pubescence is present, but not prominent. Some younger leaves display moderate. |
| Leaf Basal Thickness: | $\bar{x}$ = 7.28 mm<br>range: 5.0–9.0 mm |
| Leaf Distance Between Serrations: | $\bar{x}$ = 42.97 mm<br>range: 25.0–72.0 mm |
| Petiole Length: | $\bar{x}$ = 24.12 cm<br>range: 20.1–31.5 cm |
| Petiole Width: | $\bar{x}$ = 2.97 cm<br>range: 2.6–3.4 cm |
| DISEASE RESISTANCE: | No observations made |

GENERAL OBSERVATIONS

This new artichoke cultivar is a unique type that exhibits the following characteristics. The plants moderate height, ranging from 132–165 cm. Its comparative head qualities to California's artichoke variety Green Globe include: green (non-glossy) exterior coloration, comparable head numbers. Head numbers ranging from 5–11 heads per plant. Head shape does vary displaying a pronounced flat, spherical shape. These non-glossy heads are produced in the sizes ranging from (18) primary, size (36) secondaries and size (60) tertiaries. Floral stalk development and head numbers can vary. Anthocyanin coloration is present in innermost interior bracts and found on only some outer, exterior bract edges. Its presence is characterized as light. The head spinosity is slightly more prominent on these notched bracts. The average spine length ranges between 1.0–3.0 mm. The plants upright growth habit is intermediate, but is very vigorous. The canopies coloration is a deeper green/green/yellow color with some colors ranging towards darker green/green/grey hues. These colors on Munsell Leaf Color Chart range from 5 GY 3/4–5 GY 4/4–5 GY 3/6. Leaf spinosity is light to moderate, categorized as few. Floral stalk development during anthesis produces a purple flower. Flower color varies with flower maturity. The phenotypic characteristics of this cultivar may vary slightly, depending upon variation in the environmental factors. Including weather (temperature, humidity and light intensity), day length, soil type, farming practices, location and time of year.

I claim:

1. A new and distinct cultivar of artichoke plant named 'PS-MSC0003', as described and illustrated.

* * * * *

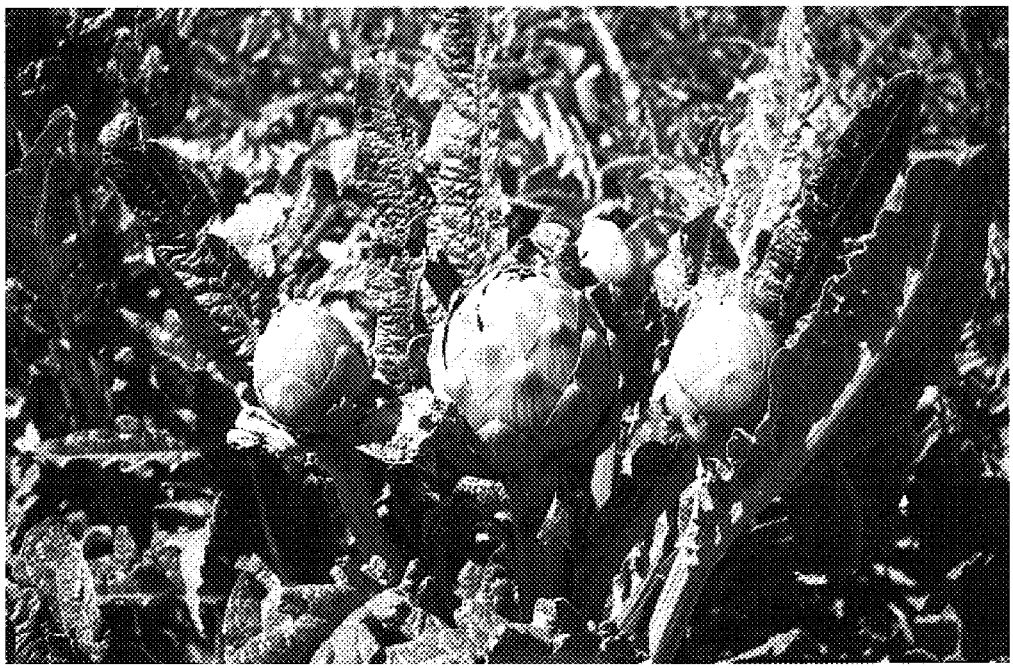

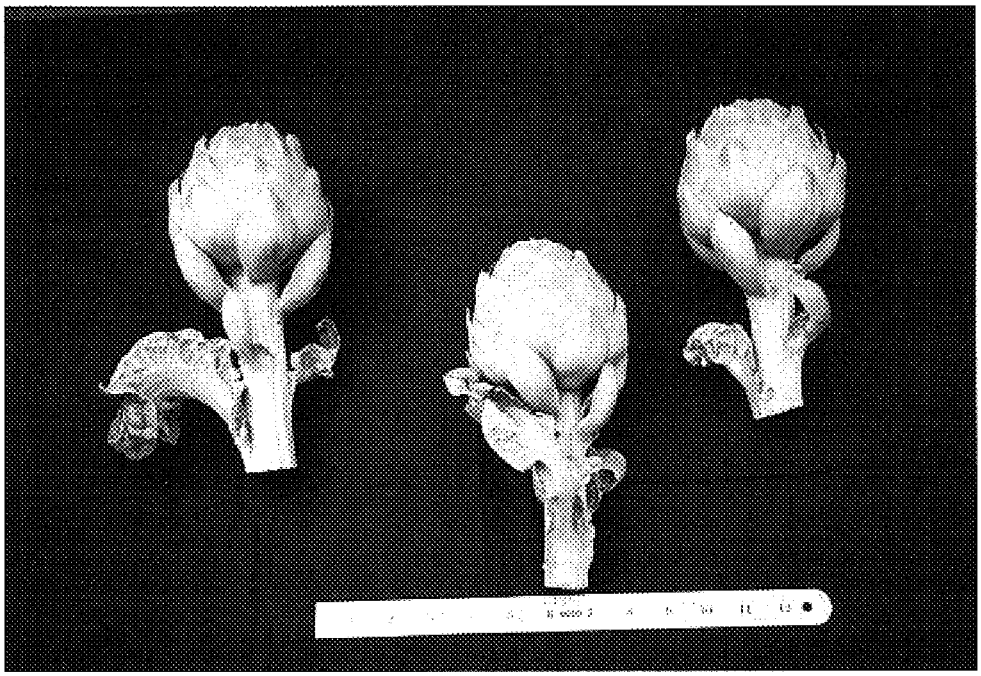

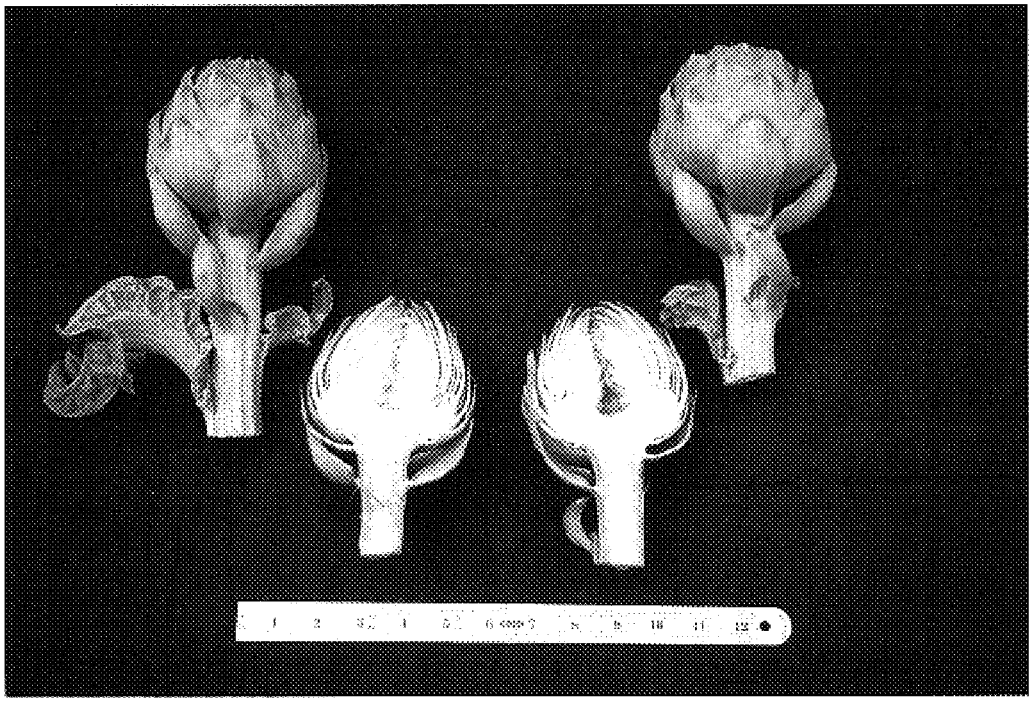

UNITED STATES PATENT AND TRADEMARK OFFICE

CERTIFICATE OF CORRECTION

PATENT NO. : PP 14,578 P2
DATED : March 9, 2004
INVENTOR(S) : William J. Colfer

It is certified that error appears in the above-identified patent and that said Letters Patent is hereby corrected as shown below:

Title page,
Item [73], Assignee, should read -- Seed Research Services, LLC, Salinas, CA (US) --.

Signed and Sealed this

First Day of June, 2004

JON W. DUDAS
*Acting Director of the United States Patent and Trademark Office*